United States Patent [19]

Weier

[11] 4,069,219
[45] Jan. 17, 1978

[54] 7ξ-(ALKOXYCARBONYL)-6ξ-ALKYL/HALO-17-HYDROXY-3-OXO-17α-PREGN-4-ENE-21-CARBOXYLIC ACID γ-LACTONES AND CORRESPONDING 21-CARBOXYLIC ACIDS, THEIR SALTS, AND ESTERS

[75] Inventor: Richard M. Weier, Deerfield, Ill.
[73] Assignee: G. D. Searle & Co., Chicago, Ill.
[21] Appl. No.: 754,136
[22] Filed: Dec. 27, 1976
[51] Int. Cl.$^2$ .............................................. C07J 19/00
[52] U.S. Cl. ............................ 260/239.57; 260/397.1; 260/397.5
[58] Field of Search .................................. 260/239.57

[56] References Cited

U.S. PATENT DOCUMENTS

| | | | |
|---|---|---|---|
| 3,787,396 | 1/1974 | Weier | 260/239.57 |
| 3,972,871 | 8/1976 | Karim et al. | 260/239.57 |

*Primary Examiner*—Elbert L. Roberts
*Attorney, Agent, or Firm*—John M. Brown

[57] ABSTRACT

Various preparations and the diuretic activity of 7ξ-(alkoxycarbonyl)-6ξ-alkyl/halo-17-hydroxy-3-oxo-17α-pregn-4-ene-21-carboxylic acid γ-lactones and corresponding 21-carboxylic acids, their salts, and esters are disclosed.

5 Claims, No Drawings
}

7ξ-(ALKOXYCARBONYL)-6ξ-ALKYL/HALO-17-HYDROXY-3-OXO-17α-PREGN-4-ENE-21-CARBOXYLIC ACID γ-LACTONES AND CORRESPONDING 21-CARBOXYLIC ACIDS, THEIR SALTS, AND ESTERS

This invention relates to 7ξ-(alkoxycarbonyl)-6ξ-alkyl/halo-17-hydroxy-3-oxo-17α-pregn-4-ene-21-carboxylic acid lactones and corresponding 21-carboxylic acids, their salts and esters, and to processes for the preparation thereof. More particularly, this invention provides lactones of the formula

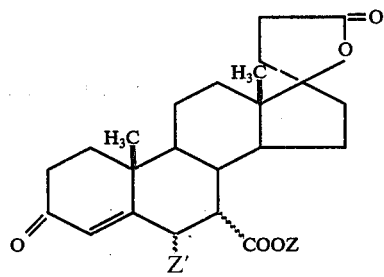

and corresponding 21-carboxylic acids, their salts, and esters of the formula

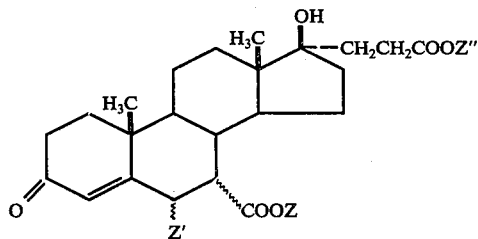

wherein Z represents alkyl; Z' represents deuterium, halogen, or alkyl; and Z" represents hydrogen, alkali metal, alkaline-earth metal/2, ammonium, or alkyl; and the wavy lines signify that the substituents in positions 6 and 7 of the steroid nuclei can be in either alpha or beta configuration, alike or different. Those skilled in the art will recognize that the term "alkaline-earth metal/2" is dictated by the fact that such metals are divalent, whereas the other substituents represented by Z" are monovalent; and when, for example, Z" represents Ca/2 in formula II, the contemplated salts are more conventionally depicted by the formula

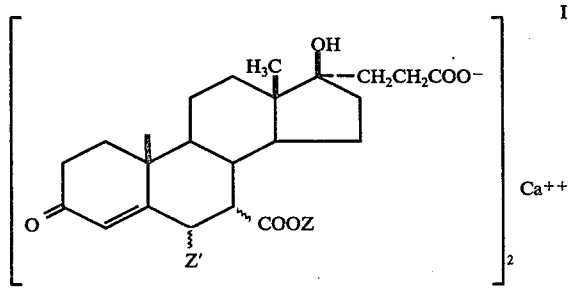

wherein Z, Z', and the wavy lines retain the meanings previously assigned.

Among the alkyls represented by Z and Z", those of fewer than 8 carbons are preferred, which is to say methyl, ethyl, 1-methylethyl, 1,1-dimethylethyl, propyl, 1-methylpropyl, 2-methylpropyl, 2,2-dimethylpropyl, butyl, pentyl, 4-methylpentyl, hexyl, 3-methylhexyl, heptyl, and like monovalent, saturated, acyclic, straight- or branched- chain, hydrocarbon groupings of empirical formula $$-C_nH_{2n+1}$$

wherein n represents a positive integer less than 8. The alkyls represented by Z' are likewise preferably of fewer than 8 carbons, but arranged in straight chains only. Among such primary (1°) alkyls, methyl and ethyl are especially advantageous.

The halogens represented by Z' are fluorine, chlorine, bromine, and iodine, among which those of atomic number less than 53 are preferred.

The alkali and alkaline-earth metals represented by Z" are preferably, but not necessarily exclusively, those of atomic number greater than 4 and less than 37 (i.e., sodium, magnesium, potassium, and calcium).

Equivalent to the compounds disclosed herein, for the purposes of this invention, are solvates thereof in which functionally insignificant amounts of solvent are present.

The foregoing compounds are useful by reason of their valuable biological properties. Thus, for example, they are diuretic: They reverse the effects of desoxycorticosterone acetate (DCA) on urinary sodium and potassium.

The capacity of the instant compounds to reverse the renal electrolyte effects of DCA can be demonstrated via the following standardized test, substantially as described by C. M. Kagawa in chapter 34 of volume II of "Evaluation of Drug Activities: Pharmacometrics," edited by D. R. Laurence and A. L. Bacharach: A group (Group I) of 8 male Charles River rats, each weighing between 150 and 200 gm, is adrenalectomized and maintained thereafter on sugar cubes and tap water ad libitum overnight. Each animal is thereupon subjected to these successive treatments: (a) 0.012 mg of DCA dissolved in 0.1 ml or corn oil is injected subcutaneously; (b) 2.4 mg of test compound dissolved or suspended in 0.5 ml of corn oil or other physiologically inert solvent (e.g., aqueous 0.9% sodium chloride) is administered subcutaneously or intragastrically; (c) 2.5 ml of aqueous 0.9% sodium chloride is injected subcutaneously. Urinary sodium and potassium are measured by customary techniques on samples of urine collected during the 4 hr. immediately following treatment. Controls are provided by second and third groups of 16 and 8 150–200 gm rats each, respectively, concurrently and identically treated excepting that in Group II, 0.33 mg of spironolactone is substituted for the test compound and the solution thereof is injected subcutaneously, while in Group III neither test compound nor spironolactone is administered. DCA produces sodium (Na) retention, loss of potassium (K), and a corresponding reduction in the mean log Na × 10/K. Spironolactone serves as an index of the validity of the test, the dose of 0.33 mg having been shown [Hofmann et al., Arch. intern. pharmacodynamie, 165, 476 (1967)] to induce a 50% reversal of the effects of the DCA. Kagawa [Endocrinology, 74, 724 (1964)] reported a standard error of ±0.84 per 4-rat response, determined from a large number of tests and based on 60 degrees of freedom, for the mean log Na × 10/K measurement. From this it can be calculated that the least significant difference (P < 0.05) in mean log Na × 10/K between 2 groups of 8 rats each is ± 0.168. It follows that when mean log Na × 10/K for Group I is equal to or greater than that for Group II, and the latter in turn exceeds the value for Group III by at least 0.168 log units, the reversals of the renal electrolyte effects of DCA represented thereby are significant. A compound active at the 2.4 mg dose level is retested at lower doses until the median effective dose (MED), a dose in mg sufficient to produce a 50% inhibition of the renal electrolyte effects of the DCA administered, can be calculated. The subcutaneous MED of 17-hydroxy-7α-(methoxycarbonyl)-6α-methyl-3-oxo-17α-pregn-4-ene-21-carboxylic acid γ-lactone in the foregoing test was found to be 0.20 mg. This activity is specified merely for purposes of illustration, and is accordingly not to be construed as either delimiting or exclusionary.

Those skilled in the art will recognize that observations of activity in standardized tests for particular biological effects are fundamental to the development of valuable new drugs, both veterinary and human.

Compounds of formula I wherein Z' represents β-deuterium can be prepared by enol etherifying a compound (disclosed and claimed in U.S. Pat. No. 3,787,396) of the formula

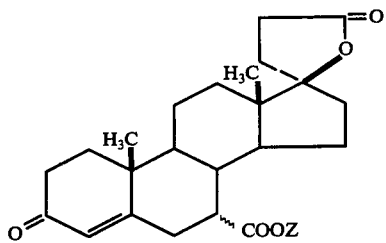

IV wherein Z and the wavy line retain the meanings previously assigned (for example, by contacting it — in the presence of a catalytic amount of a strong acid such as 4-methylbenzenesulfonic, perchloric or hydrochloric acid — with (a) a trialkoxymethane and corresponding alkanol or (b) a 2,2-dialkoxypropane) to produce the corresponding dienol ether

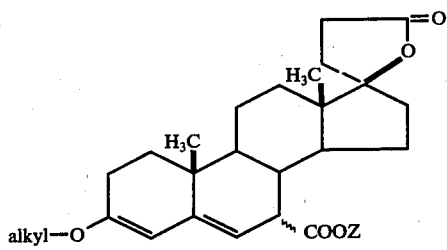

V which, in turn, is selectively hydrolysed and deuterated (for example, by contacting it with hydrogen-d chloride and water-$d_2$ in 1,1-bis[2-methoxyethane]). When the etherifying agent is a 2,2-dialkoxypropane, etherification is commonly carried out in a solvent such as benzene, 4-methylbenzene, N,N-dimethylformamide, or 1,4-dioxane.

Compounds of formula I wherein Z' represents α-halogen can be prepared by (1) enol esterifying a compound of formula IV (for example, by (a) contacting it with 1-propen-2-yl acetate in the presence of a catalytic amount of a strong acid such as 4-methylbenzenesulfonic or sulfuric acid, (b) heating it in benzene solution with acetic anhydride in the presence of a catalytic amount of 48% hydrobromic acid, or (c) heating it with acetic anhydride and acetyl chloride) to produce the corresponding dienol acetate

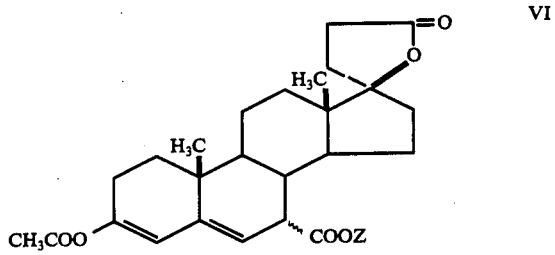

VI (2) reductively deacetylating a compound of formula VI (for example, by heating it with sodium tetrahydroborate(1-) in a mixture of methanol and 1,1'-oxybis[2-methoxyethane]) to produce the corresponding 5-en-3β-ol

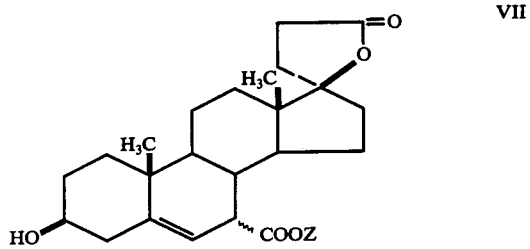

VII (3) 5,6-dihalogenating a compound of formula VII (for example, by contacting it with chlorine or bromine in a solvent such as acetic acid) to produce the corresponding 5α,6β-dihalo compound

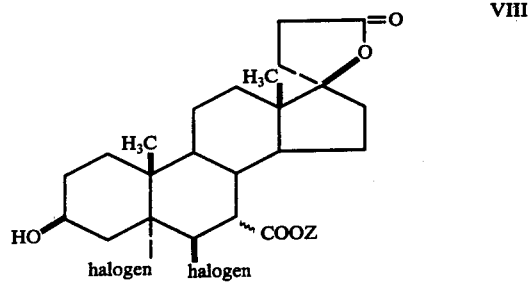

VIII (4) epimerizing the halogens in a compound of formula VIII (for example, by allowing the compound to stand in a solvent such as chloroform, carbon tetrachloride, or dichloromethane) to produce the corresponding 5β,6α-dihalo compound

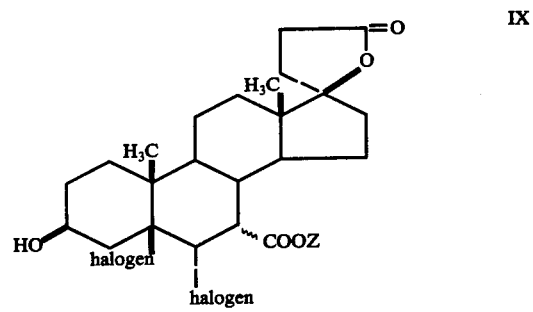

IX and (5) oxidizing the 3β-hydroxyl in a compound of formula IX to oxo (for example, by contacting a benzene solution of the compound with a solution of chromium oxide in aqueous acetic acid), then selectively dehydrohalogenating the resultant 3-oxo-5,6-dihalo compound (for example, by heating it in situ with aqueous alkali acetate).

Compounds of formula I wherein Z' represents fluorine can be prepared by contacting a compound of formula V with perchloryl fluoride in a solvent such as pyridine, aqueous 1,4-dioxane, or tetrahydrofuran. The 6β-fluoro compound which results can be converted to the 6α-epimer by conventional means (for example, by contacting the compound with hydrogen chloride in cold chloroform containing a small amount of ethanol).

Compounds of formula I wherein Z' represents β-bromine can be prepared by contacting a compound of formula VI with 1-bromo-2,5-pyrrolidinedione and sodium acetate in a cold mixture of acetic acid, 2-propanone, and water.

Compounds of formula I wherein Z' represents methyl can be prepared by (1) subjecting a compound of formula V to the Vilsmeier-Haack procedure (for example, using phosphoryl chloride and N,N-dimethylformamide), thereby producing the corresponding 6-formyl compound

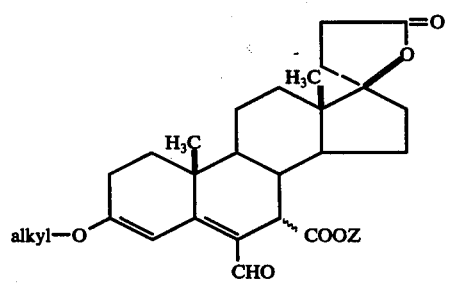

(2) selectively reducing the formyl grouping in a compound of formula X [for example, by contacting the compound with lithium hydrotris (1,1-dimethylethoxy) aluminate] to produce the corresponding 6-hydroxymethyl compound

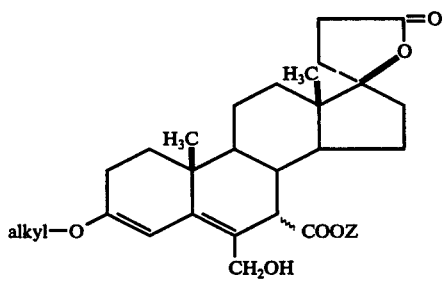

(3) selectively hydrolyzing a compound of formula XI and dehydrating the product (for example, by contacting the dienol ether in aqueous with hydrogen chloride) to produce the corresponding 6-methylene compound

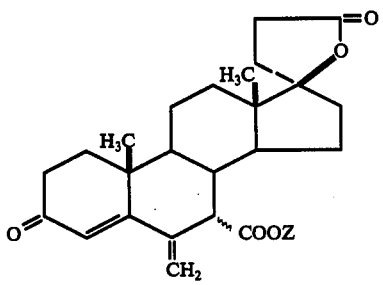

and (4) stereoselectively reducing the methylene in a compound of formula XII (for example, by hydrogenating the compound in tetrahydrofuran, using palladium-on-charcoal as a catalyst, or by hydrogenating the compound in a mixture of benzene and ethanol, using chlorotris(triphenylphosphine)rhodium as a catalyst. In the first instance, a 6α-methyl product eventuates, whereas in the second — which requires that the 7-substituent be in alpha configuration — the corresponding 6β-methyl product is obtained.)

Compounds of formula I wherein Z' represents primary alkyl can be prepared by (1) acetylating the 3β-hydroxyl in a compound of formula VII (for example, by contacting the compound with acetic anhydride in pyridine solution) to produce the corresponding ester

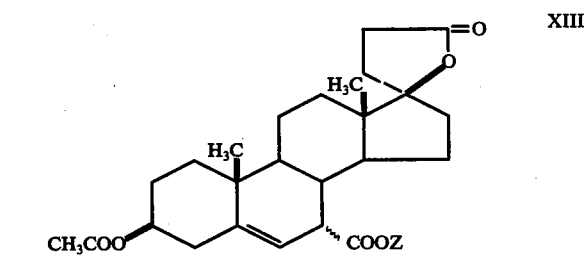

(2) 5α,6α-epoxidizing a compound of formula XIII (for example, by contacting it in cold dichloromethane with a peroxy acid such as benzenecarboperoxoic, 3-chlorobenzenecarboperoxoic, or 2-carboxybenzenecarboperoxic acid) to produce the corresponding oxirane

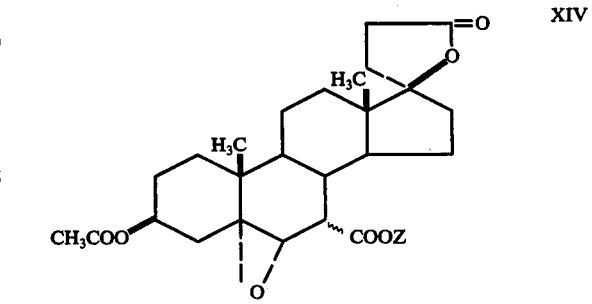

(3) contacting a compound of formula XIV in a solvent medium with an organometalic reagent capable of nucleophilic displacement of the epoxy grouping by alkyl (for example, lithium dialkyl(1°)cuprate (1-) in a cold mixture of tetrahydrofuran and 1,1-bis[2-methoxyethane]) to produce the corresponding 5α-hydroxy-6β-alkyl compound

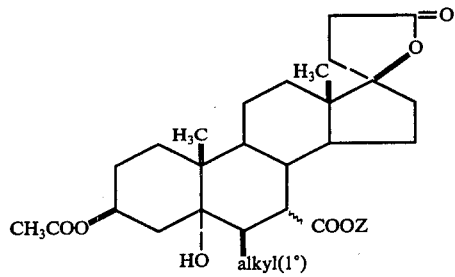

XV (4) hydrolyzing the ester grouping in a compound of formula XV (for example, by heating the compound with an alkali carbonate in aqueous methanol) to produce the corresponding 3β-ol

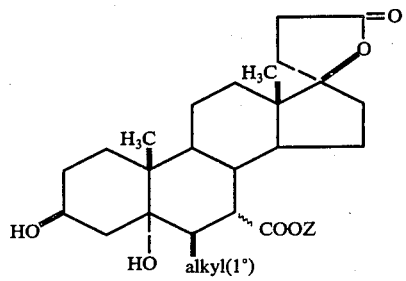

XVI (5) selectively oxidizing the 3β-hydroxyl in a compound of formula XVI to oxo (for example, by contacting a cold acetone solution of the compound with a solution of chromium oxide in aqueous sulfuric acid) to produce the corresponding 3-one

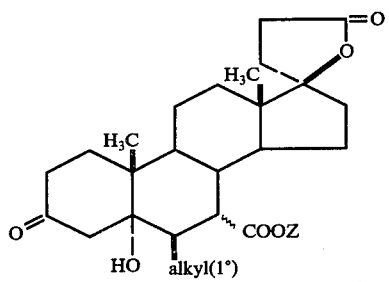

XVII (6) dehydrating a compound of formula XVII (for example, by heating a benzene solution of the compound with activated magnesium silicate) to produce the corresponding 4-en-3-one

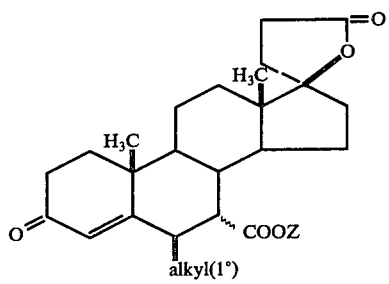

XVIII and (7) epimerizing the 6β-alkyl in a compound of formula XVIII (for example, by heating a benzene solution of the compound with neutral aluminum oxide).

Compounds of formula I wherein Z' represents primary alkyl can also be prepared by contacting a compound of formula II wherein Z' represents primary alkyl and Z" represents hydrogen, alkali metal, alkaline-earth metal/2, or ammonium with — preferably — a strong acid (for example, hydrogen chloride) in a liquid medium, the duration of contact being inversely proportional to the strength of the acid and the solubility of the formula I or II starting material in the contact medium.

Compounds of formula I wherein Z' represents primary alkyl in alpha configuration can also be prepared by (1) contacting 5α,6α-epoxy-3β,17β-dihydroxyandrostane-17-propanol α,3-diacetate [J. Org. Chem., 26, 3077 (1961)] in a solvent medium with an organometallic reagent capable of (a) nucleophilic displacement of the epoxy grouping by alkyl and (b) diesterification (for example, alkyl(1°)magnesium bromide in a warm mixture of tetrahydrofuran and 1,1-bis[2-methoxyethane]) to produce the corresponding 6β-alkyl tetraol

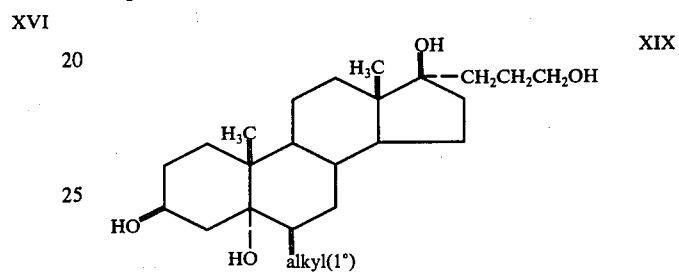

XIX (2) selectively oxidizing the primary hydroxyl in a compound of formula XIX to carboxyl and the 3β-hydroxyl therein to oxo, (for example, by contacting a 2-propanone solution of the compound with a solution of chromium oxide in aqueous sulfuric acid) to produce the corresponding γ-lactone.

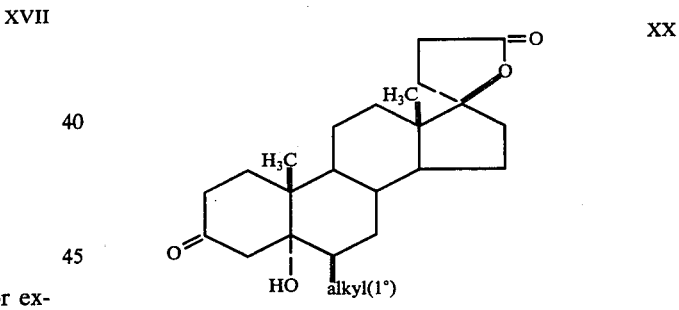

XX (3) dehydrating a compound of formula XX (for example, by heating a benzene solution of the compound with activated magnesium silicate) to produce the corresponding 4-en-3-one

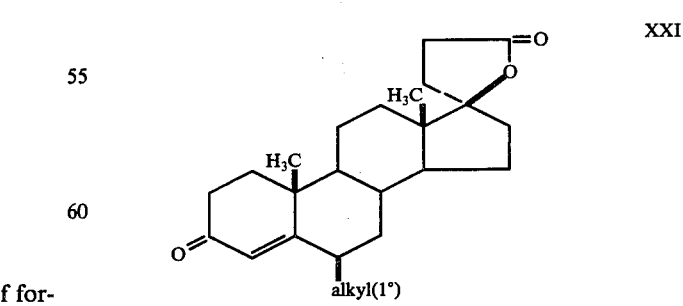

XXI (4) epimerizing the 6β-alkyl in a compound of formula XXI (for example, by heating a benzene solution of the compound with neutral aluminum oxide) to produce the corresponding 6α-alkyl compound

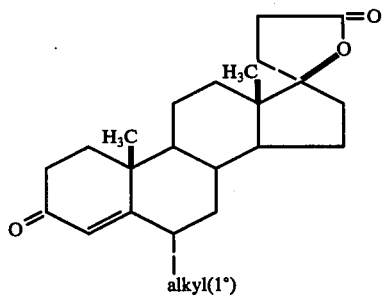

XXII (5) dehydrogenating a compound of formula XXII (for example, by heating it with 2,3,5,6-tetrachloro-2,5-cyclohexadien-1,4-dione in the presence of a strong acid such as 4-methylbenzenesulfonic acid, using dimethylbenzene as solvent) to produce the corresponding 4,6-dien-3-one

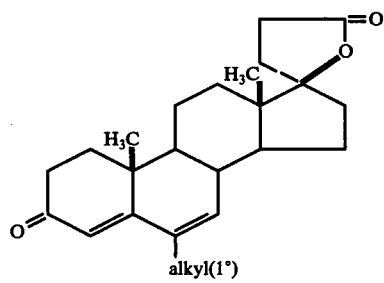

XXIII (6) biscyanating a compound of formula XXIII (for example, by heating it with an alkali metal cyanide in aqueous methanol buffered by ethyl acetate) to produce, via spontaneous intramolecular condensation and tautomerization, the corresponding enamine

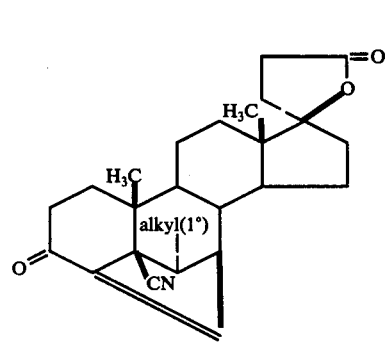

XXIV (7) hydrolyzing the enamine grouping in a compound of formula XXIV (for example, by heating the compound with dilute mineral acid) to produce the corresponding β-diketone

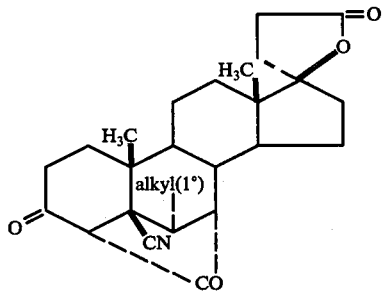

XXV and (8) cleaving a β-diketone of formula XXV under esterifying and dehydrogenating conditions (for example, by heating the compound with an alkali metal alkoxide optionally formed in situ from an alkali metal and an alkanol), then lactonizing the product (for example, by acidifying with mineral acid).

Compounds of formula II wherein Z' represents primary alkyl and Z" represents alkali metal or alkalineearth metal/2 can be prepared by contacting a compound of formula I wherein Z' represents primary alkyl, or a compound of formula II wherein Z' represent primary alkyl and Z" represents hydrogen, with an appropriate base in a solvent medium (for example, the hydroxide of an alkali or alkalineearth metal or — where the starting material is a formula II compound aforesaid — the bicarbonate of an alkali metal, using aqueous alkanol in which the alkoxy constituent is identical with that present in the formula I or II starting material as a solvent).

Compounds of formula II wherein Z' represents primary alkyl and Z" represents hydrogen can be prepared by briefly contacting a compound of formula II wherein Z' represents primary alkyl and Z" represents alkali metal, alkaline-earth metal/2, or ammonium with a proton source in a liquid medium (for example, hydrogen chloride or other acid in water).

Compounds of formula II wherein Z' represents primary alkyl and Z" represents ammonium can be prepared by contacting a compound of formula II wherein Z' represents primary alkyl and Z" represents hydrogen with ammonia in a solvent medium (for example, 2-propanol).

Compounds of formula II wherein Z' represents primary alkyl and Z" represents alkyl can be prepared by conventional esterifying procedures (for example, contacting a compound of formula II wherein Z' represents primary alkyl and Z" represents alkali metal with an alkyl halide in the presence of bicarbonate buffer, using a solvent such as N,N-dimethylformamaide as the contact medium).

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted. Specific rotations are for chloroform solutions at room temperatures, referred to the D line of sodium.

EXAMPLE 1

To a solution of 46 parts of 3-ethoxy-17-hydroxy-7α-(methoxycarbonyl)-17α-pregna-3,5-diene-21-carboxylic acid γ-lactone (U.S. 3,972,871) and 238 parts of 1,1'-oxybis(2-methoxy)ethane is added approximately 100 parts of a 2% solution of hydrogen-d chloride in water-d₂. The oily precipitate which forms in the resultant mixture is dissolved by warming the mixture briefly, whereupon it is allowed to cool to room temperature over 1 hour. The white needles which crystallize out are separated by filtration and air-dried. The product thus isolated is 17-hydroxy-7α-(methoxycarbonyl)-3-oxo-17α-pregn-4-ene-21-carboxylic-6β-d acid γ-lactone melting at 191°–193° and having a specific rotation of +27°. The product has the formula

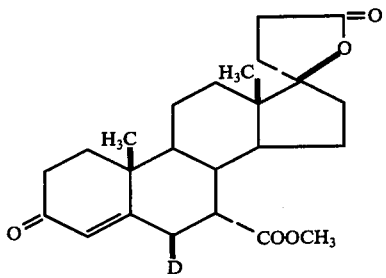

EXAMPLE 2

A. A solution of 9 parts of 17-hydroxy-7α-[(1-methylethoxy)carbonyl-3-oxo-17α-pregn-4-ene-21-carboxylic acid γ-lactone (U.S. 3,787,396) and 2 parts of 4-methylbenzenesulfonic acid monohydrate in 460 parts of 1-propen-2-yl acetate is stirred at room temperatures for 24 hours, during which volatile components are thrice removed by vacuum distillation and replaced with equal volumes of 1-propen-2-yl acetate. The resultant mixture is poured into a vigorously-stirred mixture of 435 parts of methylbenzene and 1000 parts of a saturated aqueous solution of sodium bicarbonate, whereupon the methylbenzene phase is separated and the aqueous phase is extracted with methylbenzene. The two methylbenzene solutions are combined into one, which is consecutively washed with aqueous 5% potassium bicarbonate and a saturated aqueous solution of sodium chloride, then stripped of solvent by vacuum distillation. The residue is 3-(actyloxy)-17-hydroxy-7α-[(1-methylethoxy)carbonyl]-17α-pregn-3,5-diene-21-carboxylic acid γ-lactone.

B. To a solution of 10 parts of 3-(acetyloxy)-17-hydroxy-7α-[(1-methylethyoxy)carbonyl]-17-α-pregna-3,5-diene-21-carboxylic acid γ-lactone in 320 parts of methanol and 70 parts of 1,1'-oxybis[2-methoxyethane] at the boiling point under reflux is added, during 30 minutes, a solution of 4 parts of sodium tetrahydroborate(1−) in 80 parts of methanol. Heating at the boiling point under reflux is continued for 3 hours after the addition is complete, whereupon the reaction mixture is cooled and 50 parts of water then introduced. Volatile solvents are removed from the resultant mixture by vacuum distillation at 35°–40°, and the residue is partitioned between dichloromethane and water. The dichloromethane phase is separated, dried over anhydrous sodium sulfate, and stripped of solvent by vacuum distillation, affording 3β,17-dihydroxy-7α-[(1-methylethoxy)-carbonyl]-17α-pregn-5-ene-21-carboxylic acid γ-lactone as the residue.

C. To a solution of 50 parts of 3β,17-dihydroxy-7α-[(1-methylethoxy)carbonyl]-17α-pregn-5-ene-21-carboxylic acid γ-lactone in 350 parts of 1,1'-oxybis[2-methoxyethane] at room temperature is slowly added a solution of 25 parts of bromine and 250 parts of acetic acid. Crystals precipitate. The precipitate is filtered off, consecutively wshed with acetic acid and water, and dried in air. The material thus isolated is 5,6β-dibromo-3β,17-dihydroxy-7α-[(1-methylethoxy)carbonyl]-5α,-17α-pregnane-21-carboxylic acid γ-lactone, which can be further purified by crystallization from methanol.

D. A solution of 10 parts of 5,6β-dibromo-3β,17-dihydroxy-7α-[(1-methylethoxy)carbonyl]-5α,17α-pregnane-21-carboxylic acid γ-lactone in 150 parts of chloroform is allowed to stand at room temperature for 3 days, whereupon solvent is removed by vacuum distillation at 25°–30°. The residue is fractionally crystallized from methanol. The first crop of crystals is the starting steriod; succeeding crops are 5,6α-dibromo-3β,17-dihydroxy-7α-[(1-methylethoxy)-carbonyl]-5β,17α-pregnane-21-carboxylic acid γ-lactone, which can be further purified by crystallization from methanol.

E. To a suspension of 4 parts of 5,6α-dibromo-3β,17-dihydroxy-7α-[(1-methylethoxy)carbonyl]-5β,17α-pregnane-21-carboxylic acid γ-lactone in 40 parts of benzene is added, with stirring at room temperature, a solution of 1 part of chromium oxide in a mixture of 12 parts of acetic acid and 6 parts of water. Stirring at room temperature is continued for 6 hours after the addition is complete, whereupon the benzene plase — in which is dissolved the 5β,6α-dibromo-17-hydroxy-17α-[(1-methylethoxy)carbonyl]-3-oxo-17α-pregnane-21-carboxylic acid γ-lactone produced — is separated, washed with water, and stirred at the boiling point under reflux for 6 hours with a solution of 2 parts of potassium acetate in 20 parts of water. The benzene phase is then separated, washed with water, dried over anhydrous sodium sulfate, and stripped of solvent by vacuum distillation. The residue is 6α-bromo-17-hydroxy-7α-[(1-methylethoxy)carbonyl]-3-oxo-7α-pregn-4-ene-21-carboxylic acid γ-lactone, which can be further purified by crystallization from a mixture of dichloromethane and 1,1'-oxybis[2-methoxyethane]. The product has the formula

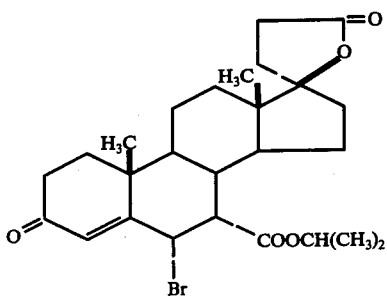

EXAMPLE 3

A. To a slurry of 150 parts of 17-hydroxy-6β-[(1-methylethoxy)carbonyl]-3-oxo-17α-pregn-4-ene-21-carboxylic acid γ-lactone (U.S. 3,787,396) in 134 parts of 1,1',1''-[methylidynetris(oxy)]trisethane and 235 parts of ethanol is added, with stirring, 10 parts of 4-methylbenzenesulphonic acid. Stirring is continued for approximately 15 minutes after the addition is complete — until the reaction mixture becomes homogeneous. At this point 40 parts of anhydrous sodium acetate and 20 parts of pyridine is stirred in. The resultant mixture is stripped of volatile components by vacuum distillation, whereupon the residue is triturated with ethyl acetate. Insoluble material is filtered out; and the filtrate is freed of ethyl acetate by vacuum distillation, affording 3-ethoxy17-hydroxy-7β-[(1-methylethoxy)carbonyl]-17α-pregna-3,5-diene-21-carboxylic acid γ-lactone as the residue.

B. Perchloryl fluoride is bubbled through a stirred solution of 1 part of 3-ethoxy-17-hydroxy-7β-[(1-methylethoxy)carbonyl]-17α-pregna-3,5-diene-21-carboxylic acid γ-lactone in 15 parts of pyridine at −20° for 3 minutes. The resultant mixture is poured into 150 parts of ice-water. The gummy precipitate which forms is extracted into dichloromethane. The dichloromethane extract is washed with water, dried over anhydrous sodium sulfate, and stripped of solvent by vacuum distialltion, affording as the residue 6β-fluoro-17-hydroxy-7β-[(1-methylethoxy)carbonyl]-3-oxo-17α-pregn-4-ene21-carboxylic acid 65-lactone, which can be further purified by chromatographing on silica gel, using benzene and ethyl acetate as developeing solvents.

C. Anhydrous hydrogen chloride is bubbled through a solution of 3 parts of 6β-fluoro-17β-[(1-methylethoxy)carbonyl]-3-oxo-17α-pregn-4-ene-21-carboxylic acid γ-lactone in 1800 parts of chloroform and 7 parts of ethanol at 0° for 1½ hours. The resultant mixture is neutralized by washing with aqueous 5% sodium carbonate, then washed with water, dried over anhydrous sodium sulfate, and stripped of solvent by vacuum distillation. The residue is 6α-fluoro-17-hydroxy-7β-[(1-methylethoxy)carbonyl]-3-oxo-17α-pregn-4-ene-21-carboxylic acid γ-lactone, which can be further purified by crystallization from a mixture of ethyl acetate and hexane. The product has the formula

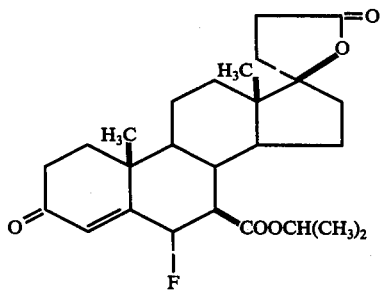

EXAMPLE 4

A. Substitution of 9 parts of 17-hydroxy-7α-(methoxycarbonyl)-3-oxo-17α-pregn-4-ene-21-carboxylic acid γ-lactone (U.S. Pat. No. 3,787,396) for the 17-hydroxy-7α-[(1-methylethoxy)carbonyl]-3-oxo-17α-pregn-4-ene21-carboxylic acid γ-lactone called for in Example 2A affords, by the procedure there detailed, 3-(acetyloxy)-17-hydroxy-7α-(methoxycarbonyl)-17α-pregna-3,5-diene-21-carboxylic acid γ-lactone. The product, upon recrystallization from methanol, melts at 226°–231°.

B. To a solution of 30 parts of sodium acetate and 100 parts of acetic acid in 2000 parts of aqueous 30% 2-propanone is added, with stirring at 0°, 44 parts of 3-(acetyloxy)-17-hydroxy-7α-(methoxycarbonyl)-17α-pregna3,5-diene-21-carboxylic acid γ-lactone, followed by 20 parts of 1-bromo-2,5-pyrrolidinedione. Stirring is continued at 0° for 1 hour after the additions are complete, whereupon 3000 parts of water is introduced and the crystalline precipitate which forms is filtered off and dried in air. Recrystallization of this material from a mixture of dichloromethane and 1,1'-oxybis[2-methoxyethane] affords 6β-bromo-17-hydroxy-7α-(methoxycarbonyl)-3-oxo-17α-pregn4-ene-21-carboxylic acid γ-lactone as a colorless substance melting at 168°–170° (with decomposition), and further characterized by a specific rotation of −11°. The product has the formula

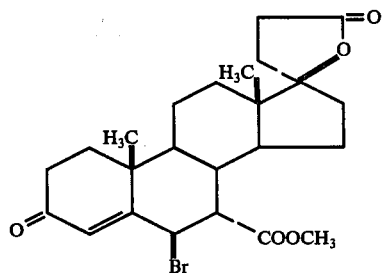

EXAMPLE 5

A. Approximately 31 parts of phosphoryl chloride is slowly stirred into 190 parts of N,N-dimethylformamide at 0°, followed 5 minutes later by a solution of 29 parts of 3-ethoxy-17-hydroxy-7α-(methoxycarbonyl)-17α-pregna3,5-diene-210carboxylic acid γ-lactone (U.S. Pat. No. 3,972,871) in 35 parts of N,N-dimethylformamide. The reaction mixture, originally colorless, becomes dark red. Stirring is continued for 2 hours at 0°, whereupon the mixture is allowed to warm to room temperatures with continued stirring overnight. The resultant mixture is poured into 1500 parts of aqueous 7% sodium acetate. The mixture thus obtained is stirred for 2 hours, at which point the yellow precipitate which has formed is filtered out, air-dried, and recrystallized from methanol to give 3-ethoxy-6-formyl17-hydroxy-7α-(methoxycarbonyl)-17α-pregna-3,5-diene-21-carboxylic acid γ-lactone hemihydrate, melting at 226°–228° and further characterized by a specific rotation of −281°. Water of crystallization can be removed by heating the product in vacuo at arount 80°.

B. To a solution of 22 parts of lithium hydrotris(1,1-dimethylethoxy)aluminate in 360 parts of tetrahydrofuran at 0° is added, with stirring, 22 parts of 3-ethoxy-6-formyl-17-hydroxy-7α-(methoxycarbonyl)-17α-pregna-3,5-diene-21-carboxylic acid γ-lactone hemihydrate. The steroid promptly dissolves. Stirring is continued for 4½ hours while the reaction mixture is allowed to warm to room temperature. Approximately 200 parts of water is then stirred in, followed by sufficient acetic acid to bring the pH to 8–9. Solvent is removed by vacuum distillation, and the residue is slurried with ethyl acetate. The slurry is filtered through diatomaceous earth. The filtrate, dried over anhydrous sodium sulfate and stripped of solvent by vacuum distillation, affords 3-ethoxy-17-hydroxy-6-(hydroxymethyl)-7α-(methoxycarbonyl)-17α-pregna3,5-diene-21-carboxylic acid γ-lactone as the residue, a colorless solid foam.

C. Approximately 150 parts of a 2.4:1 mixture of 2-propanone and water is adjusted to a pH in the range 1.5-2.0 with 1% hydrochloric acid, whereupon 2 parts of 3-ethoxy-17-hydroxy-6(hydroxymethyl)-7α-(methoxycarbonyl)-17α-pregna-3,5-diene-21-carboxylic acid γ-lactone is added and the resultant mixture stirred for 45 minutes at room temperatures. Volatile components are thereupon removed by vacuum distillation at room temperature; and the gummy precipitate which forms in the distilland is separated by filtration, washed with water, air-dried, and chromatographed in hexane solution on silica gel, using hexane and mixtures thereof with increasing amounts of ethyl acetate as developing solvent. From an eluate comprising 40% ethyl acetate in hexane, on evaporation of solvent, 17-hydroxy-7α-(methoxycarbonyl)-6-methylene-3-oxo-17α-pregn-4-ene-21-carboxylic acid γ-lactone is obtained as the residue. The product, further purified by washing with 1,1'-oxybis[2-methoxyethane] and drying in air, melts at approximately 165°–166°. It has a specific rotation of +216°.

D. A solution of 100 parts of 17-hydroxy-7α-(methoxycarbonyl)-6-methylene-3-oxo-17α-pregna-4-ene-21-carboxylic acid γ-lactone in 25,000 parts of tetrahydrofuran is hydrogenated at atmospheric pressure, using 7 parts of pre-reduced 5% palladium-on-charcoal as catalyst. When, after approximately 2½ hours, hydrogen uptake indicates that the contemplated reduction is complete, catalyst is filtered out; and the filtrate is stripped of solvent by vacuum distillation. The residue, a white foam, crystallizes on trituration with 1,1'-oxybis[2-methoxyethane]. The crystalline material is separated and recrystallized from methanol, affording 17-hydroxy-7α-(methoxycarbonyl)-6α-methyl-3-oxo-17α-pregna-4-ene-21-carboxylic acid γ-lactone melting at 191°–194.5° and having a specific rotation of +11°. The product has the formula

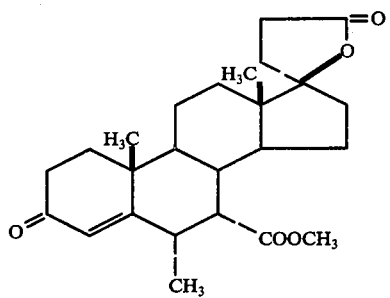

EXAMPLE 6

A solution of 1 part of 17-hydroxy-7α-(methoxycarbonyl)-6-methylene-3-oxo-17α-pregn-4-ene-21-carboxylic acid γ-lactone in 160 parts of a 4.5:1 mixture of benzene and ethanol is hydrogenated at atmospheric pressure, using 1 part of chlorotris(triphenylphosphene)rhodium as catalyst. When the uptake of hydrogen indicates that reduction of the methylene group is complete (after approximately 6½ hours), catalyst is filtered out; and the filtrate is stripped of solvent by vacuum distillation. The residual red gum is chromatographed in dichloromethane solution on silica gel, using dichloromethane and mixtures thereof with increasing amounts of ethyl acetate as developing solvents. From an eluate comprising 11% of ethyl acetate in dichloromethane, on evaporation of solvent and recrystallization of the residue from methanol, 17-hydroxy-7α-(methoxycarbonyl)-6β-methyl-3-oxo-17α-pregn-4-ene-21-carboxylic acid γ-lactone melting at 222°–224° is obtained. The product has a specific rotation of +4° and the formula

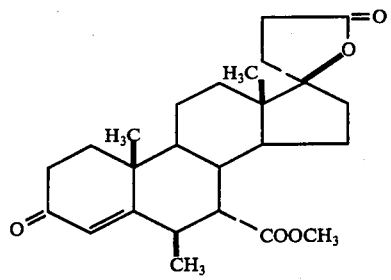

EXAMPLE 7

A. Substitution of 9 parts of 17-hydroxy-7β-[(1-methylethoxy)carbonyl]-3-oxo-17α-pregn-4-ene-21-carboxylic acid γ-lactone (U.S. Pat. No. 3,787,396) for the 7-epimer thereof called for in Example 2A affords, by the procedure there detailed, 3-(acetyloxy)-17-hydroxy-7β-[(1-methylethoxy)carbonyl]-17α-pregna-3,5-diene-21-carboxylic acid γ-lactone.

B. Substitution of 10 parts of 3-(acetyloxy)-17-hydroxy-7β-[(1-methylethoxy)carbonyl]-17α-pregna-3,5-diene-21-carboxylic acid γ-lactone for the 7α-epimer called for in Example 2B affords, by the procedure there detailed, 3β,17-dihydroxy-7β-[(1-methylethoxy)carbonyl]-17α-pregn-5-ene-21-carboxylic acid γ-lactone.

C. A mixture of 10 parts of 3β,17-dihydroxy-7β-[(1-methylethoxy)carbonyl]-17α-pregn-5-ene-21-carboxylic acid γ-lactone, 20 parts of acetic anhydride, and 100 parts of pyridine is allowed to stand at room temperatures overnight, then poured into 300 parts of ice-water. The resultant mixture is extracted with dichloromethane. The dichloromethane extract is washed with water, dried over anhydrous sodium sulfate, and stripped of solvent by vacuum distillation. The residue, a white gum, is 3β-(acetyloxy)-17-hydroxy-7β-[(1-methylethoxy)carbonyl]-17α-pregn-5-ene-21-carboxylic acid γ-lactone, which can be further purified by chromatography on silica gel, using benzene and mixtures thereof with increasing amounts of ethyl acetate as developing solvent.

D. To a solution of 9 parts of 3β-(acetyloxy)-17-hydroxy-7β-[(1-methylethoxy)carbonyl]-17α-pregn-5-ene-21-carboxylic acid γ-lactone in 335 parts of dichloromethane is added, with stirring at 0°, a solution of 4 parts of 85% 3-chlorobenzenecarboperoxoic acid in 65 parts of dichloromethane. Stirring at 0° is continued for 1 hour after the addition is complete, and thereafter for a further 23 hours at room temperatures. The resultant mixture is diluted with 2 volumes of dichloromethane. The mixture thus obtained is consecutively washed with aqueous 10% sodium sulfite, aqueous 5% potassium bicarbonate (until no more carbon dioxide is evolved), and water, then dried over anhydrous sodium sulfate and stripped of solvent by vacuum distillation. The residue, 3β-(acetyloxy)-5,6α-epoxy-17-hydroxy-7β-[(1-methylethoxy)carbonyl]-5α,17α-pregnane-21-carboxylic acid γ-lactone, can be further purified by crystallization from methanol.

E. To a suspension of 39 parts of copper (1+) iodide in 1800 parts of anhydrous tetrahydrofuran at 0° under nitrogen is added, with stirring, a solution of 15 parts of ethyllithium in 225 parts of 1,1'-oxybisethane. Stirring at 0° under nitrogen is continued for 30 minutes, whereupon a solution of 100 parts of 3β-(acetyloxy)-5,6α-epoxy-17-hydroxy-7β-[(1-methylethoxy)carbonyl]-5α,-17α-pregnane-21-carboxylic acid γ-lactone in 450 parts of anhydrous tetrahydrofuran is introduced. Stirring at 0° under nitrogen is continued for 8 hours, at which point the reaction mixture is poured into 2000 parts of a saturated aqueous solution of ammonium chloride. The organic phase is separated, the aqueous phase is extracted with dichloromethane, and the resultant extract is combined with the organic phase. The solution thus obtained is washed with water, dried over anhydrous sodium sulfate, and stripped of solvent by vacuum distillation. The residue is 3β-(acetyloxy)-6β-ethyl-5,17-dihydroxy-7β[(1-methylethyl)carbonyl]-5α,17α-pregnane-21-carboxylic acid γ-lactone, which can be further purified by chromatographing on silica gel, using hexane and mixtures thereof with increasing amounts of ethyl acetate as developing solvents.

F. A solution of 1 part of 3β-(acetyloxy)-6β-ethyl-5,17-dihydroxy-7β[(1-methylethyl)carbonyl]-5α,17α-pregnane-21-carboxylic acid γ-lactone in 50 parts of methanol is heated at the boiling point under reflux for 3 hours with 10 parts of aqueous 5% potassium bicarbonate. Organic solvents is thereupon removed by vacuum distillation, and the aqueous residue is acidified with glacial acetic acid. The resultant mixture is stirred for 1 hour at room temperatures, then extracted with dichloromethane. The dichloromethane extract is consecutively washed with aqueous 5% potassium bicarbonate and water, dried over anhydrous sodium sulfate, and stripped of solvent by vacuum distillation. The 6β-ethyl-3β,5,17-trihydroxy-7β-[(1-methylethoxy)carbonyl]-5α,17α-pregnane-21-carboxylic acid γ-lactone thus isolated can be further purified by chromatographing on silica gel, using hexane and mixtures thereof with increasing amounts of ethyl acetate as developing solvents.

G. To a solution of 45 parts of 6β-ethyl-3β,5,17-trihydroxy-7β-[(1-methylethoxy)carbonyl]-5α,17α-pregnane21-carboxylic acid γ-lactone in 475 parts of 2-propanone is added, with stirring at 0°, 47 parts of a mixture prepared by dissolving 100 parts of chromium oxide in 200 parts of water and consecutively adding thereto 150 parts of sulfuric acid and 200 parts of water. The resultant mixture is diluted with 1 volume of water. The mixture thus obtained is stripped of acetone by vacuum distillation. The white solid which precipitates in the distilland is filtered out, washed with water, and air-dried. The product thus isolated is 6β-ethyl-5,17-dihydroxy-7β-[(1-methylethoxy)carbonyl]-3-oxo-5α,-17α-pregnane-21-carboxylic acid γ-lactone, which can be further purified by crystallization from methanol.

H. To a solution of 2 parts of 6β-ethyl-5,17-dihydroxy-7β-[(1-methylethoxy)carbonyl]-3-oxo-5α,17α-pregnane-21-carboxylic acid γ-lactone in 350 parts of benzene is added 20 parts of activated magnesium silicate. The resultant mixture is heated at the boiling point with stirring for 4 hours, then filtered. The filtrate is stripped of solvent by vacuum distillation, leaving 6β-ethyl-17-hydroxy-7β-[(1-methylethoxy)carbonyl]-3-oxo-17α-pregn-4-ene-21-carboxylic acid γ-lactone as the residue. The product can be further purified by crystallization from methanol. It has the formula

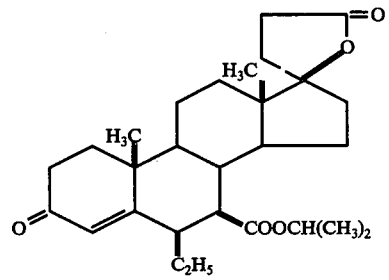

EXAMPLE 8

A solution of 1 part of 6β-ethyl-17-hydroxy-7β-[(1-methylethoxy)carbonyl]-3-oxo-17α-pregn-4-ene-21-carboxylic acid γ-lactone in 175 parts of benzene is stirred at the boiling point under reflux with 10 parts of neutral aluminum oxide for 30 minutes. The mixture is then filtered, and the filtrate is stripped of solvent by vacuum distillation. The residue is 6α-ethyl-17-hydroxy-7β-[(1-methylethoxy)carbonyl]-3-oxo-17α-pregn-4-ene-21-carboxylic acid γ-lactone, which can be further purified by crystallization from methanol or a mixture of hexane and ethyl acetate. The product has the formula

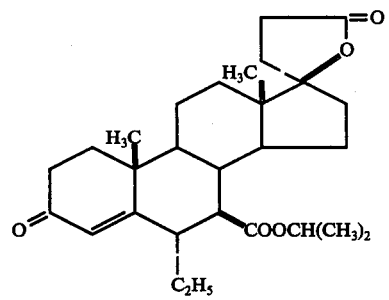

EXAMPLE 9

A. To a solution of 8 parts of ethylmagnesium bromide in 16 parts of 1,1'-oxybis[2-methoxyethane] is slowly added, with stirring, a solution of 10 parts of 5α,6α-epoxy-3β,17β-dihydroxyandrostane-17-propanol α,3-diacetate [J. Org. Chem., 26, 3077 (1961)] in 60 parts of tetrahydrofuran. The resultant mixture is stirred and distilled until the temperature of the escaping vapors reaches 59°, whereupon the distilland is stirred at the boiling point under reflux for 18 hours. It is then cooled and then mixed with 500 parts of ice. The mixture thus obtained is extracted with dichloromethane. The dichloromethane extract is consecutively washed with 5% hydrochloric acid and water, dried over anhydrous sodium sulfate, and stripped of solvent by vacuum distillation. The residue is 6β-ethyl-3β,5α,17β-trihydroxyandrostane-17-propanol, which can be further purified by crystallization from aqueous methanol.

B. To a solution of 1 part of 6β-ethyl-3β,5α,17β-trihydroxyandrostane-17-propanol in 40 parts of acetone at 0° is slowly added, with stirring, 4 parts of a mixture prepared by dissolving 100 parts of chromium oxide in 200 parts of water and consecutively adding thereto 150 parts of sulfuric acid and 200 parts of water. The resultant mixture is diluted with 1 volume of water. The mixture thus obtained is stripped of solvents by vacuum distillation. The colorless solid which precipitates in the distilland is filtered off, washed with after, and dried in air. The product thus isolated is 6β-ethyl-5,17-dihydroxy-3-oxo-17α-pregnane-21-carboxylic acid γ-lactone, which can be further purified by crystallization from methanol.

C. To a solution of 2 parts of 6β-ethyl-5,17-dihydroxy-3-oxo-17α-pregnane-21-carboxylic acid γ-lactone in 350 parts of benzene is added 20 parts of activated magnesium silicate. The resultant mixture is stirred at the boiling point under reflux for 4 hours, then filtered. The filtrate is stripped of solvent by vacuum distillation. The residue is 6β-ethyl-17-hydroxy-3-oxo-17α-pregn-4-ene-21-carboxylic acid γ-lactone, which can be further purified by crystallization from aqueous acetone.

D. A mixture of 10 parts of neutral aluminum oxide with a solution of 1 part of 6β-ethyl-17-hydroxy-3-oxo-17β-pregn-4-ene-21-carboxylic acid γ-lactone in 175 parts of benzene is stirred at the boiling point under reflux for 30 minutes, then filtered. The filtrate is stripped of solvent by vacuum distillation. The residue is 6α-ethyl-17-hydroxy-3-oxo-17α-pregn-4-ene-21-carboxylic acid γ-lactone, which can be further purified by crystallization from aqueous methanol.

E. A solution of 43 parts of 6α-ethyl-17-hydroxy-3-oxo-17α-pregn-4-ene-21-carboxylic acid γ-lactone, 40 parts of 2,3,5,6-tetrachloro-2,5-cyclohexadiene-1,4-dione, 1 part of 4-methylbenzenesulfonic acid monohydrate, and 3500 parts of a mixture of dimethylbenzenes is heated at the boiling point under reflux for 3½ hours. The resultant mixture is chromatographed on silica gel, using benzene and mixtures thereof with increasing amounts of ethyl acetate as developing solvents. From an eluate comprising 15% ethyl acetate in benzene, on evaporation of solvent and recrystallization of the residue from a mixture of hexane and ethyl acetate, 6-ethyl-17-hydroxy-3-oxo-17α-pregna-4,6-diene-21-carboxylic acid γ-lactone is obtained.

F. A solution consisting of approximately 55 parts of 6-ethyl-17-hydroxy-3-oxo-17α-pregna-4,6-diene21-carboxylic acid γ-lactone, 50 parts of potassium cyanide, 72 parts of ethyl acetate, 454 parts of methanol, and 160 parts of water is heated at the boiling point under reflux with stirring for 4½ hours, then allowed to stand at room temperatures overnight. Organic solvents are thereupon removed by vacuum distillation, the oily residue is diluted with 500 parts of water, and the pH of the resultant mixture is adjusted to 7 by slowly introducing 20% hydrochloric acid. Hydrogen cyanide is evolved, and precipitation occurs. The precipitate is filtered off, dried in air, and taken up in ethyl acetate. The ethyl aceate solution is extracted with 20% hydrochloric acid. Residual ethyl acetate is removed from the extract by bubbling nitrogen therethrough. The extract is thereupon cooled to 0° and then neutralized with sodium hydroxide. The resultant precipitate is filtered off, washed well with water, and air-dried. The product thus isolated is 7α,4-aminomethylidyne-5-cyano-6α-ethyl-17-hydroxy-3-oxo5β,17α-pregnane-21-carboxylic acid γ-lactone, which can be further purified by crystallization from acetone.

G. A solution consisting of 23 parts of 7α,4-aminomethylidyne-5-cyano-6α-ethyl-17-hydroxy-3-oxo-5β,17α-pregnane-21-carboxylic acid γ-lactone in 350 parts of 3% hydrochloric acid is heated at 90°-95° with occasional stirring for 4½ hours, then cooled. Insoluble solids are separated by filtration, washed to neutrality with water, and dried in air. The product thus isolated is 4α,7α-carbonyl-5-cyano-6α-ethyl-17-hydroxy-3-oxo-5β,17α-pregnane-21-carboxylic acid γ-lactone, which can be further purified by recrystallization from 2-propanol.

H. To 185 parts of sodium metal is added 4200 parts of 2-propanol at a rate such that rapid refluxing is maintained. When the addition is complete, refluxing is continued for 3 hours via external heating, whereupon 14,200 parts of 2-propanol followed by 210 parts of 4α,7α-carbonyl-5-cyano-6α-ethyl-17-hydroxy-3-oxo-5β,17α-pregnane-21-carboxylic acid γ-lactone is introduced. The resultant solution is heated at the boiling point under reflux with stirring in a nitrogen atmosphere for 22 hours, at which point solvent is removed by vacuum distillation. The oily residue is taken up in 4,000 part of water. The aqueous solution is diluted with 4,000 parts of acetone, and the resultant mixture is acidified with 10% hydrochloric acid. After 30 minutes, the acetone is removed by vacuum distillation; and the residue is extracted with ethyl acetate. The extract is washed well with aqueous 5% potassium bicarbonate and then with water, next consecutively dried over magnesium sulfate and sodium sulfate, and finally stripped of solvent by vacuum distillation. The resultant oil is dissolved in a minimum amount of hot methanol. Colorless 6α-ethyl-17-hydroxy-7α-[(1-methylethoxy)carbonyl]-3-oxo-17α-pregn-4-ene-21-carboxylic acid γ-lactone crystallizes out of the methanol solution on cooling. The product is separated by filtration and dried in air.

The mother liquor is chromatographed on silica gel, using benzene and mixtures thereof with increasing amounts of ethyl acetate as developing solvent. From an eluate comprising approximately 15% ethyl acetate in benzene, on evaporation of solvent and recrystallization of the residue from methanol, 6α-ethyl-17-hydroxy-7β-[(1-methylethoxy)carbonyl]-3-oxo-17α-pregn-4-ene-21-carboxylic acid γ-lactone is obtained. This product has the formula

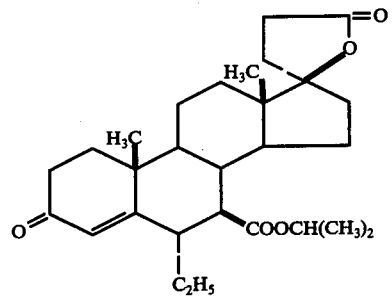

EXAMPLE 10

To a slurry of 2 parts of 17-hydroxy-7α-(methoxycarbonyl)-6β-methyl-3-oxo-17α-pregn-4-ene-21-carboxylic acid γ-lactone in 40 parts of methanol is added 5 parts of aqueous 4% sodium hydroxide, whereupon the resultant mixture is warmed briefly to 40° to effect disolution. The solution is allowed to stand at room temperatures under nitrogen overnight, then stripped of the bulk of the solvents present by vacuum distillation. Sufficient ethanol is added to, and distilled from, the distilland to remove remaining water azeotropically. The solid residue is washed by slurrying with ethyl acetate and dried in air. The product thus isolated is sodium 17-hydroxy-7α-(methoxycarbonyl)-6β-methyl- 3-oxo-17α-pregn-4-ene-21-carboxylate, having the formula

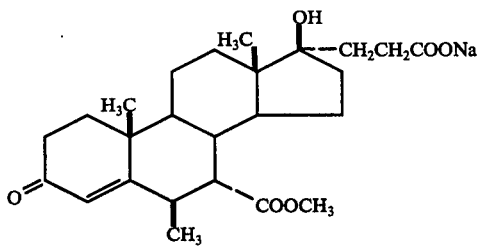

EXAMPLE 11

To a slurry of 3 parts of 17-hydroxy-7α-(methoxycarbonyl)-6β-methyl-3-oxo-17α-pregn-4-ene-21-carboxylic acid γ-lactone in 60 parts of methanol is added 10 parts of aqueous 4% potassium hydroxide. The resultant mixture is heated briefly at not to exceed 40° until solution is effected. The solution is allowed to stand at room temperatures under nitrogen overnight, then stripped of the bulk of the solvents present by vacuum distillation. Sufficient ethanol is added to, and distilled from, the distilland to remove the remaining water. The residue is slurried with ethyl acetate and dried in air. The product thus isolated is potassium 17-hydroxy-7α-(methoxycarbonyl)-6β-methyl-3-oxo-17α-pregn-4-ene-21-carboxylate. It has the formula

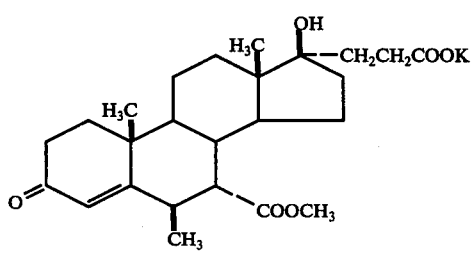

EXAMPLE 12

To a solution of 1 part of potassium 17-hydroxy-7α-(methoxycarbonyl)-6β-methyl-3-oxo-17α-pregn-4-ene-21-carboxylate in 70 parts of water is added 20 parts of 5% hydrochloric acid. The resultant precipitate is filtered out, washed with water, and dried in air. The product thus isolated is 17-hydroxy-7α-(methoxycarbonyl)-6β-methyl-3-oxo-17α-pregn-4-ene-21-carboxylic acid, having the formula

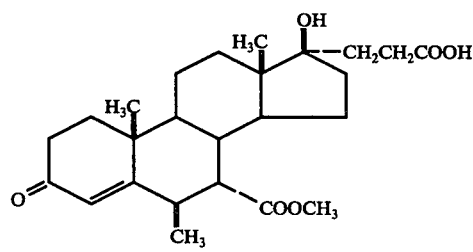

EXAMPLE 13

A mixture of 206 parts of 17-hydroxy-7α-(methoxycarbonyl)-6β-methyl-3-oxo-17α-pregn-4-ene-21-carboxylic acid, 19 parts of calcium hydroxide, and 4000 parts of methanol is stirred at 40° under nitrogen for 2 hours. Solvent is then removed by vacuum distillation, and the residue is crystallized from ethyl acetate. The product thus isolated is calcium bis[17-hydroxy-7α-(methoxycarbonyl)-6β-methyl-3-oxo-17α-pregn-4-ene-21-carboxylate,], having the formula

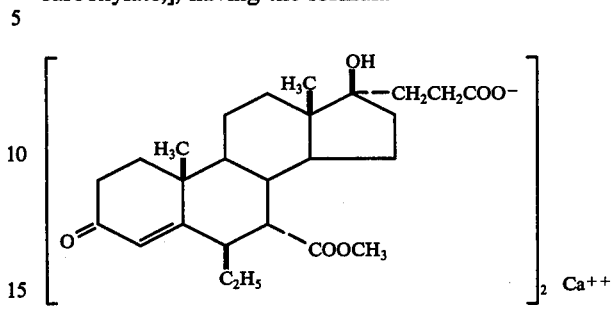

EXAMPLE 14

To 20 parts of 2-propanol, saturated with ammonia, is added 1 part of 17-hydroxy-7α-(methoxycarbonyl)-6β-methyl-3-oxo-17α-pregn-4-ene-21-carboxylic acid. The resultant mixture is allowed to stand at room temperatures for 24 hours, at which point solvent is removed by vacuum distillation. The residue is washed with ethyl acetate and dried in air. The product thus isolated is ammonium 17-hydroxy-7α-(methoxycarbonyl)-6β-methyl-3-oxo-17α-pregn-4-ene-21-carboxylic acid, having the formula

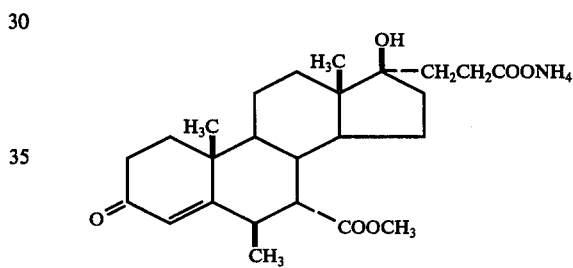

EXAMPLE 15

To a slurry of 6 parts of 6α-ethyl-17-hydroxy-7α-[(1-methylethoxy)carbonyl]-3-oxo-17α-pregn-4-ene-21-carboxylic acid γ-lactone in 120 parts of methanol is added 13 parts of aqueous 4% sodium hydroxide, whereupon the resultant mixture is briefly warmed to effect dissolution. The solution is allowed to stand at room temperatures under nitrogen overnight, then stripped of the bulk of the solvents by vacuum distillation. Sufficient ethanol is added to, and distilled from, the distilland to remove the remaining water. The residue is sodium 6α-ethyl-17-hydroxy-7α-[(1-methylethoxy)carbonyl]-3-oxo-17α-pregn-4-ene-21-carboxylate, which can be further purified by slurrying with ethyl acetate and air-drying. The product has the formula

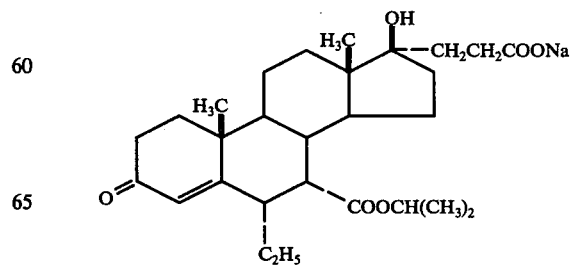

EXAMPLE 16

Substitution of 6 parts of 6β-ethyl-17-hydroxy-7β-[(1-methylethoxy)carbonyl]-3-oxo-17α-pregn-4-ene-21-carboxylic acid γ-lactone for the 6α-ethyl-17-hydroxy-7α-[(1-methylethoxy)carbonyl]-3-oxo-17α-pregn-4-ene-21-carboxylic acid γ-lactone called for in Example 15 affords, by the procedure there detailed, sodium 6β-ethyl-17-hydroxy-17β-[(1-methylethoxy)carbonyl]-3-oxo-17α-pregn-4-ene-21-carboxylate. The product has the formula

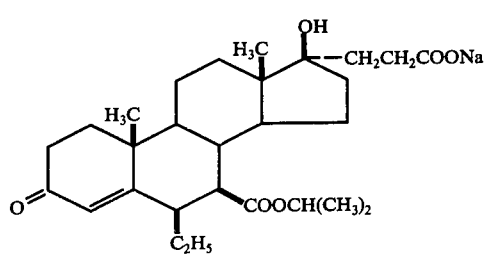

EXAMPLE 17

Substitution of 6 part of 6α-ethyl-17-hydroxy-7β-[(1-methylethoxy)carbonyl]-3-oxo-17α-pregn-4-ene-21-carboxylic acid γ-lactone and 18 parts of aqueous 4% potassium hydroxide for the 6α-ethyl-17-hydroxy-7α-[(1-methylethoxy)carbonyl]-3-oxo-17α-pregn-4-ene-21-carboxylic acid γ-lactone and aqueous 4% sodium hydroxide, respectively, called for in Example 15 affords, by the procedure there detailed, potassium 6α-ethyl-17-hydroxy-7β-[(1-methylethoxy)carbonyl]-3-oxo-17α-pregn-4-ene-21-carboxylate, having the formula

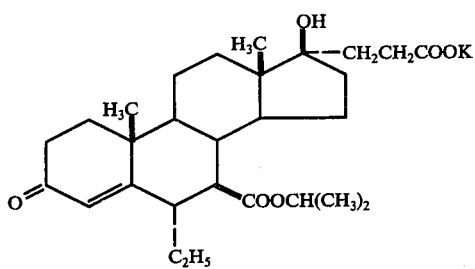

EXAMPLE 18

Substitution of 1 part of potassium 6α-ethyl-17-hydroxy-7β-[(1-methylethoxy)carbonyl]-3-oxo-17α-pregn-4-ene-21-carboxylate for the potassium 17-hydroxy-7α-(methoxycarbonyl)-6β-methyl-3-oxo-17α-pregn-4-ene-21-carboxylate called for in Example 12 affords, by the procedure there detailed, 6α-ethyl-17-hydroxy-7β-[(1-methylethoxy)carbonyl]-3-oxo-17α-pregn-4-ene-21 -carboxylic acid, having the formula

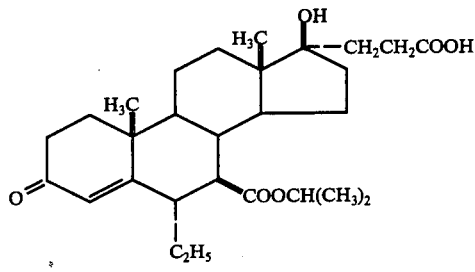

EXAMPLE 19

To a slurry of 49 parts of potassium 17-hydroxy-7α-(methoxycarbonyl)-6β-methyl-3-oxo-17α-pregn-4-ene-21-carboxylate and 63 parts of potassium bicarbonate in 950 parts of N,N-dimethylformamide is added 228 parts of methyl iodide. The resultant mixture is stirred at room temperatures for 2 hours in a nitrogen atmosphere, then poured into approximately 12,000 parts of ice-water. The gummy white precipitate which forms is separated by decanting the supernatant liquors therefrom, washed with water by decantation, and taken up in ethyl acetate. The ethyl acetate solution is washed with water, dried over anhydrous sodium sulfate, and stripped of solvent by vacuum distillation. The residue is methyl 17-hydroxy-7α-(methoxycarbonyl)-6β-methyl-3-oxo-17α-pregn-4-ene-21-carboxylate, having the formula

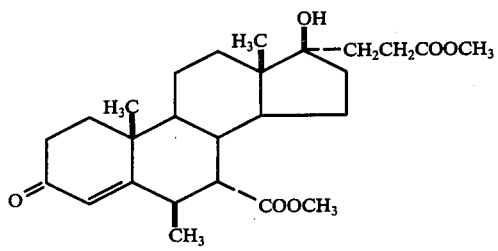

EXAMPLE 20

Substitution of 49 parts of potassium 6α-ethyl-17-hydroxy-7β-[(1-methylethoxy)carbonyl]-3-oxo-17α-pregn-4-ene-21-carboxylate and 228 parts of 1-(methylethyl)iodide for the potassium 17-hydroxy-7α-(methoxycarbonyl)-6β-methyl-3-oxo-17α-pregn-4-ene-21-carboxylate and methyl iodide, respectively, called for in Example 19 affords, by the procedure there detailed, 1-(methylethyl) 6α-ethyl-17-hydroxy-7β-[(1-methylethyl)carbonyl]-3-oxo-17α-pregn-4-ene-21-carboxylate, having the formula

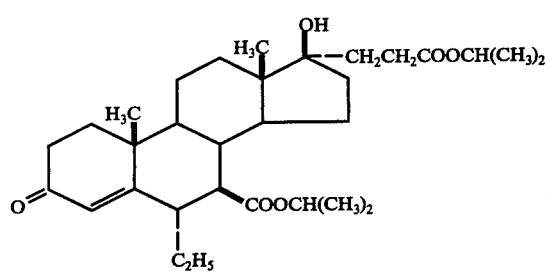

What is claimed is:
1. A compound having the formula

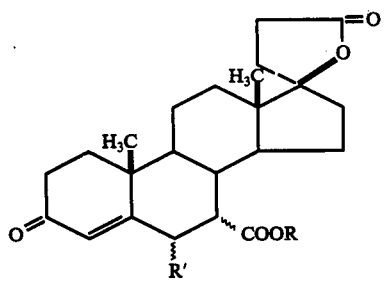

wherein R represents alkyl of fewer than 8 carbons, R' represents halogen of atomic number less than 53, and the wavy lines signify that the substituents in positions 6 and 7 of the steroid nucleus can be in either alpha or beta configuration, alike or different.

2. A compound according to claim 1 having the formula

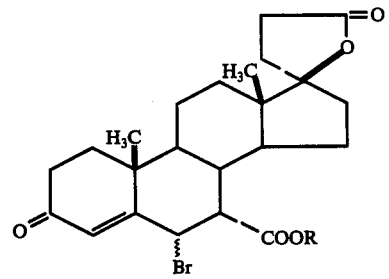

wherein R represents alkyl of fewer than 8 carbons and the wavy line signifies that the 6-bromo substituent can be in either alpha or beta configuration.

3. A compound according to claim 1 which is 6β-bromo-17-hydroxy-7α-(methoxycarbonyl)-3-oxo-17α-pregn-4-ene-21-carboxylic acid γ-lactone.

4. A compound which is 3-ethoxy-6-formyl-17-hydroxy-7α-(methoxycarbonyl)-17α-pregna-3,5-diene-21-carboxylic acid γ-lactone hemihydrate.

5. A compound which is 17-hydroxy-7α-(methoxycarbonyl)-6-methylene-3-oxo-17α-pregn-4-ene-21-carboxylic acid γ-lactone.

* * * * *